United States Patent [19]  
Ohta

[11] 4,082,750  
[45] Apr. 4, 1978

[54] TRINITRO-11H-INDENO[1,2-b]QUINOXA-LINE-11-ONE AND PROCESS FOR PREPARING SAME

[75] Inventor: Masafumi Ohta, Tokyo, Japan

[73] Assignee: Ricoh Co., Ltd., Tokyo, Japan

[21] Appl. No.: 734,183

[22] Filed: Oct. 20, 1976

[30] Foreign Application Priority Data

Oct. 27, 1975 Japan .................................. 50-128366

[51] Int. Cl.² .............................................. C07D 241/42
[52] U.S. Cl. .............................. 260/250 Q; 96/1.5 R; 96/1.6; 252/501
[58] Field of Search .................................. 260/250 Q

[56] References Cited

PUBLICATIONS

"Nitration of Hydrocarbons and Other Organic Substances", Topchiev, 1959, pp. 19–30.
Triolo et al., Disc. Abs., vol. 20, p. 1597, (1960).

*Primary Examiner*—Donald G. Daus
*Assistant Examiner*—Mark L. Berch
*Attorney, Agent, or Firm*—Blanchard, Flynn, Thiel, Boutell & Tanis

[57] ABSTRACT

Trinitro-11H-indeno[1,2-b]quinoxaline-11-one obtained by further nitrating 11H-indeno[1,2-b]quinoxaline-11-one, or mononitro- or dinitro-derivatives thereof, demonstrates a conspicuous sensitization effect with respect to organic photoconductors.

3 Claims, No Drawings

TRINITRO-11H-INDENO[1,2-b]QUINOXALINE-11-ONE AND PROCESS FOR PREPARING SAME

BACKGROUND OF THE INVENTION (a) Field of the Invention

The present invention relates to a sensitizer for organic photoconductors, namely, trinitro-11H-indeno[1,2-b]quinoxaline-11-one, which has an excellent sensitization effect on organic photoconductors, together with a method of preparing that compound.

(b) Description of the Prior Art

Organic photoconductors such as, for instance, poly-N-vinyl carbazole, have recently been studied as material for use in forming the photoconductive layer of electrophotographic copying materials or image forming elements because of their superiority in film formability and transparency as well as the flexibility of the film formed thereof, but practical use thereof has so far been greatly hampered because they are much inferior to inorganic photoconductors, such as zinc oxide, in respect of photosensitivity. Therefore, in order to improve the photosensitivity of organic photoconductors, varieties of sensitizers have been used jointly therewith, but none of the sensitizers known heretofore has proved satisfactory for this purpose.

SUMMARY OF THE INVENTION

A principal object of the present invention is to eliminate the foregoing drawbacks in the prior art and to provide a novel sensitizer which can demonstrate a satisfactory sensitization effect with respect to organic photoconductors.

An additional object of the present invention is to provide a method of manufacturing trinitro-11H-indeno[1,2-b]quinoxaline-11-one.

In other words, the sensitizer according to the present invention consists of trinitro-11H-indeno[1,2-b]quinoxaline-11-one having the formula

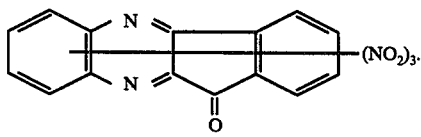

The present inventors have conducted a series of studies with a view to eliminating the aforesaid drawbacks in the prior art and found that the use of a compound having the above formula is effective in achieving the object of the present invention. The present invention is based on this finding.

Trinitro-11H-indeno[1,2-b]quinoxaline-11-one can be prepared by nitrating 11H-indeno[1,2-b]quinoxaline-11-one or mononitro- or dinitro-derivatives thereof. The nitration on this occasion is usually effected by heating the starting material 11H-indeno[1,2-b]quinoxaline-11-one or mononitro- or dinitro-derivative thereof at a temperature in the range of from 70° to 100° C in the presence of a mixed acid [i.e., a mixture of fuming nitric acid (specific gravity: 1.5 – 1.52) and concentrated sulfuric acid at the mixing ratio of 1:1 by volume]. In this context, the starting material can be readily obtained by a procedure as taught in J. Org. Chem. 27, p.1674 (1962). Hereunder will be shown an example of synthesis of trinitro-11H-indeno[1,2-b]quinoxaline-11-one.

EXAMPLE OF SYNTHESIS 24.0g of 11H-indeno[1,2-b]quinoxaline-11-one (the procedure for synthesis is in accordance with the above cited literature) were dissolved in 400 ml of a mixed acid (wherein the specific gravity of the fuming nitric acid employed was 1.50) while being cooled with ice. Then, the temperature of the resulting solution was raised gradually, and reaction was effected by maintaining it at about 70° to 80° C for 3 hours. The reaction mixture, after leaving it to cool down, was poured into a large quantity of cold water, and the resulting precipitate was separated by filtration, washed with water and dried. Subsequently, the thus treated precipitate was again dissolved in 600 ml of a mixed acid (wherein the specific gravity of the fuming nitric acid employed was 1.52), and the temperature of the resulting solution was raised gradually and maintained at 85° to 90° C for 5 hours. After further adding 180 ml of a mixed acid (wherein the specific gravity of the fuming nitric acid employed was 1.52) over about 2.5 hours' period to the solution maintained at the same temperature as above, reaction was effected for 5 hours by maintaining the temperature at about 90° to 92° C. The reaction mixture, after leaving it to cool down, was poured into a large quantity of cold water, and the resulting precipitate was separated by filtration, washed with water and dried. Subsequently, the thus treated precipitate was subjected to recrystallization by means of a benzene–acetone mixed solvent several times, whereby 2.8g of yellow plate crystals were obtained. The melting point of this crystalline compound was in the range of from 252.5° to 254.0° C. After drying this compound by heating at 110° C for 1 hour, the following analyses were conducted.

Infrared spectrum (KBr method)

There was observed absorption by the aromatic ring at 3060, 1620 and 1580 $cm^{-1}$, absorption by the carbonyl group at 1740 $cm^{-1}$, and absorption by the nitro group at 1350 $cm^{-1}$, respectively.

| Elementary analysis | C(%) | H(%) | N(%) |
|---|---|---|---|
| Calc. For $C_{15}H_5N_5O_7$: | 49.06 | 1.37 | 19.07 |
| Found: | 49.35 | 1.20 | 19.04 |

N.M.R. spectrum

Solvent: deuterio N,N-dimethyl formamide
Internal standard: tetramethyl silane

| | | relative intensity |
|---|---|---|
| 8.54 ppm: | (doublet:J=9 cps) | 1 |
| 8.72 ppm: | (doublet J=2 cps) | 1 |
| 8.82 ppm: | (doublet, doublet J=2 cps, 9 cps) | 1 |
| 9.38 ppm: | (doublet J=2 cps) | 2 |

As regards the coupling of the respective protons on this occasion, it is considered that J=2 cps represents the coupling amount protons of meta-position and J=9 cps represents the coupling amount protons of ortho-position.

From the above data obtained through N.M.R. spectrum, it is evident that the coupling of ortho-position is only one and accordingly it is a trinitro-derivative. However, the substituted position of each nitro group is not clear.

In the light of the foregoing results of analyses, the product crystal was confirmed to be trinitro-11H-indeno[1,2-b]quinoxaline-11-one.

As set forth above, the novel compound according to the present invention is useful as a sensitizer for organic photoconductors, and to cite the applicable organic photoconductors, in addition to poly-N-vinyl carbazole, there are various derivatives thereof such as brominated, chlorinated or nitrated poly-N-vinyl carbazole, polyacenaphthylene, anthracene, pyrene, pyrazoline, imidazole, etc. The appropriate amount of this sensitizer to be employed is in the range of from 0.01 to 1.30 mole or thereabouts based on 1 mole of organic photoconductor (or monomer unit in the case where said organic photoconductor is a polymer).

The sensitizer according to the present invention is, as stated above, used jointly with an organic photoconductor in the photoconductive layer of electrophotographic copying materials, image-forming elements, etc. To cite the applicable electrophotographic copying materials and image-forming elements, there are, for instance, conductive support–organic photoconductive layer; conductive support–inorganic semi-conductor layer–organic photoconductive layer; conductive support–inorganic photoconductive layer–organic photoconductive layer; conductive support–non-sensitizing organic photoconductive layer–organic photoconductive layer; or the above mentioned photoconductive layers provided with an insulating protective film formed thereon (the foregoing are electrophotographic copying materials), transparent electrode–ceramics·•macromolecular film–organic photoconductive layer–transparent electrode (an image-forming element), etc.

To prepare these copying materials or elements having a stratified construction, all of the known methods of forming are applicable. For instance, an electrophotographic copying material can be formed in the following way. That is, a photoconductive layer forming solution is prepared by dissolving an appropriate organic photoconductor and trinitro-11H-indeno [1,2-b]quinoxaline-11-one in an organic solvent such as tetrahydrofuran or dioxane, this solution on the surface of a conductive support such as paper processed for conductivity, a synthetic resin film with aluminum deposited thereon through vacuum evaporation, a metal plate (e.g., aluminum plate), etc. in a desired thickness and is dried thereafter. For the purpose of enhancing the adhesion between the support and the photoconductive layer, a binder such as polyester resin, acrylic resin, novolak resin, etc. can be further added to the photoconductive layer forming solution.

Hereunder will be explained the effect of the sensitizer according to the present invention by reference to some examples of electrophotographic copying materials employing the present sensitizer.

DESCRIPTION OF THE PREFERRED EMBODIMENTS

Example 1

| | | |
|---|---|---|
| trinitro-11H-ideno[1,2-b]quinoxaline-11-one | 730 | mg |
| poly-N-vinyl carbazole | 390 | mg |
| polyester resin | 97 | mg |
| tetrahydrofuran | 8.5 | g |

By applying a photoconductive layer forming solution having the above composition on the surface of a polyester film having aluminum deposited thereon through vacuum evaporation, by means of a doctor blade with a gap of 200μ, and drying thereafter at 60° C for 10 minutes and at 120° C for 2 minutes successively, an electrophotographic copying material having a photoconductive layer of about 10μ in thickness was prepared.

Next, this copying material was divided in two, and each half was electrified by −6 KV or 6 KV corona discharge for 20 seconds by the use of a commercial electrophotographic copying material testing device. After leaving the thus electrified halves standing in a dark place for 20 seconds, the surface potential VPo(V) thereof was measured. Subsequently, by exposing them to a tungsten lamp by setting the illumination on the surface of copying material at 20 luxes, the amount of exposure required for reducing VPo by half, to wit, E½ (lux. sec), was sought and the value of this E½ was regarded as the sensitivity of the copying materials. The values of VPo and E½ on this occasion were as follows.

| polarity of charged electricity | VPo(V) | E ½ (lux.sec) |
|---|---|---|
| − | 1,000 | 3.4 |
| + | 480 | 9.8 |

On the other hand, after charging the photoconductive layer of the copying material of the present example with negative electricity by the use of a commercial electrophotographic copying machine, an electrostatic latent image was formed thereon by exposing it through an original having an image. Then, this copying material was developed with a commercial developing powder charged with positive electricity, electrostatic transfer of image (or the process of transferring an image formed on the photoconductive layer of a copying material onto a transfer paper by charging negative electricity by way of the side whereon the transfer paper is laid) was conducted by superposing a transfer paper on the developed copying material, and subsequently the image transferred to the transfer paper was thermally fixed. The resulting fixed image was high in contrast as well as concentration, and proved to be a copy of superior quality.

Comparative Example

Through the same procedure as in Example 1 save for replacing 730 mg of trinitro-11H-indeno[1,2-b]quinoxaline-11-one with 630 mg of 2,4,7-trinitrofluorenone disclosed in the specification for U.S. Pat. No. 3,484,237, an electrophotographic copying material was prepared. Subsequently, following the method of measurement in Example 1, VPo and E½ were measured. The result was as follows.

| polarity of charged electricity | VPo(V) | E ½ (lux.sec) |
|---|---|---|
| − | 530 | 4.6 |

This result shows that the comparative copying material is lower in charged electric potential and inferior in sensitivity compared with the copying material according to the present invention.

Examples 2-4

Through the same procedure as in Example 1 save for applying trinitro-11H-indeno[1,2-b]quinoxaline-11-one, organic photoconductor, polyester resin and tetrahydrofuran as specified in the following Table-1, varieties of electrophotographic copying materials were prepared.

Table 1

| Example No. | trinitro-11H-indeno [1,2-b] quinoxaline-11-one | organic photoconductor | polyester resin | tetrahydrofuran |
|---|---|---|---|---|
| 2 | 690 mg | chlorinated poly-N-vinyl carbazole* 460 mg | — | 8.5 g |
| 3 | 520 mg | brominated poly-N-vinyl carbazole** 500 mg | 90 mg | 8.9 g |
| 4 | 190 mg | 1-bromo-pyrene formaldehyde resin 570 mg | 260 mg | 5.8 g |

(Remarks)
*A substance obtained by substituting 1 chlorine atom for 1 monomer unit of poly-N-vinyl carbazole.
**A substance obtained by substituting 1 bromine atom for 2 monomer units of poly-N-vinyl carbazole.

When VPo and E½ were measured following the method of measurement in Example 1 with respect to these copying materials, the result was as shown in the following Table-2.

Table-2

| Example No. | polarity of charged electricity | VPo(V) | E ½ (lux.sec) |
|---|---|---|---|
| 2 | — | 780 | 4.3 |
| 3 | — | 830 | 4.6 |
| 4 | — | 900 | 10.6 |

As is evident from the foregoing result, trinitro-11H-indeno[1,2-b]quinoxaline-11-one can remarkably improve the photosensitivity of organic photoconductors compared with the conventional sensitizers. Moreover, the sensitivity of organic photoconductors sensitized by the sensitizer of the present invention can stand comparison with that of inorganic photoconductors.

What is claimed is:

1. A method for preparing trinitro-11H-indeno[1,2-b]quinoxaline-11-one which comprises the steps of dissolving 11H-indeno[1,2-b]quinoxaline-11-one in a first mixture of fuming nitric acid and concentrated sulfuric acid to form a first solution, maintaining the first solution at about 70° to 80° C for a period of time effective to form a first nitrated reaction product, precipitating said first reaction product, recovering the resulting first precipitate, dissolving the first precipitate in a second mixture of fuming nitric acid and concentrated sulfuric acid to form a second solution, maintaining said second solution at about 90° to 92° C for a period of time effective to form trinitro-11H-indeno[1,2-b]-quinoxaline-11-one as a final reaction product and recovering the resulting second precipitate.

2. A method for preparing trinitro-11H-indeno[1,2-b]quinoxaline-11-one which comprises the steps of dissolving 11H-indeno[1,2-b]quinoxaline-11-one in a first mixture of fuming nitric acid having a density of about 1.50 and concentrated sulfuric acid wherein said acids are mixed in a volume ratio of about 1:1 to form a first solution, maintaining the first solution at about 70° to 80° C for about 3 hours, cooling the first solution and then pouring it into cold water, recovering the resulting first precipitate, dissolving the first precipitate in a second mixture of fuming nitric acid having a density of about 1.52 and concentrated sulfuric acid wherein said acids are mixed in a volume ratio of about 1:1 to form a second solution, maintaining the second solution at about 85° to 90° C for about 5 hours, adding more of said second mixture to said second solution and then raising the temperature of said second solution to about 90° to 92° C and maintaining said second solution at about 90° to 92° C for about 5 hours, cooling said second solution, pouring said second solution into cold water and recovering the resulting second precipitate.

3. Trinitro-11H-indeno[1,2-b]quinoxaline-11-one.

* * * * *

UNITED STATES PATENT AND TRADEMARK OFFICE
CERTIFICATE OF CORRECTION

PATENT NO. : 4 082 750
DATED : April 4, 1978
INVENTOR(S) : Masafumi Ohta

It is certified that error appears in the above-identified patent and that said Letters Patent are hereby corrected as shown below:

Column 6, line 19; after "product" insert ---, precipitating said final reaction product---.

Signed and Sealed this

Twenty-ninth Day of August 1978

[SEAL]

Attest:

RUTH C. MASON
Attesting Officer

DONALD W. BANNER
Commissioner of Patents and Trademarks